(12) United States Patent
Carmignani et al.

(10) Patent No.: US 10,107,772 B2
(45) Date of Patent: Oct. 23, 2018

(54) ELECTRONICAL DEVICE FOR MEASURING AT LEAST ONE ELECTRICAL CHARACTERISTIC OF AN OBJECT

(71) Applicant: Commissariat A L'Energie Atomique et aux Energies Alternatives, Paris (FR)

(72) Inventors: Corentin Carmignani, Grenoble (FR); Christophe Brun, Grenoble (FR); Patrick Reynaud, Murianette (FR); Emmanuel Rolland, Jarrie (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 53 days.

(21) Appl. No.: 15/132,463

(22) Filed: Apr. 19, 2016

(65) Prior Publication Data

US 2016/0377564 A1 Dec. 29, 2016

(30) Foreign Application Priority Data

Apr. 20, 2015 (FR) ...................................... 15 53533

(51) Int. Cl.
G01N 27/04 (2006.01)
G01N 27/12 (2006.01)
G01N 33/487 (2006.01)

(52) U.S. Cl.
CPC ......... G01N 27/041 (2013.01); G01N 27/122 (2013.01); G01N 27/128 (2013.01); G01N 33/48721 (2013.01)

(58) Field of Classification Search
None
See application file for complete search history.

(56) References Cited

U.S. PATENT DOCUMENTS 6,557,393 B1 * 5/2003 Gokhfeld ........... G01N 27/4071
73/23.2
2005/0023137 A1 2/2005 Bhullar et al.
(Continued)

FOREIGN PATENT DOCUMENTS

DE 295 01 233 U1 4/1995
DE 10 2011 077 875 A1 12/2012
(Continued)

OTHER PUBLICATIONS

European Search Report dated Jul. 18, 2016 in French Application No. 16165876.0 (with English translation of categories of Cited Documents).
(Continued)

*Primary Examiner* — Jermele M Hollington
*Assistant Examiner* — Suresh K Rajaputra
(74) *Attorney, Agent, or Firm* — Oblon, McClelland, Maier & Neustadt, L.L.P.

(57) ABSTRACT

An electronic device for measuring at least one electrical characteristic of an object, including a supporting base provided with at least two measuring units each including at least two sets of electrodes including electrodes, is provided. The electrodes of the sets of electrodes of the same measuring unit are interdigitated such that each electrode of one of the sets of electrodes of the measuring unit is spaced by an inter-electrode distance from an electrode, of the other of the sets of electrodes of the measuring unit, which is adjacent thereto, the electrodes differ in the features in respect of contact with the object and/or the electrode spacing thereof so as to make a differential current measurement.

17 Claims, 4 Drawing Sheets

(56) References Cited

U.S. PATENT DOCUMENTS

| | | | |
|---|---|---|---|
| 2005/0023152 A1 | 2/2005 | Surridge et al. | |
| 2011/0156727 A1 | 6/2011 | Achhammer et al. | |
| 2011/0259079 A1* | 10/2011 | Maeda ............... | G01N 15/0656 |
| | | | 73/23.33 |
| 2013/0292266 A1 | 11/2013 | Surridge et al. | |
| 2014/0283630 A1 | 9/2014 | Mourey et al. | |

FOREIGN PATENT DOCUMENTS

| | | |
|---|---|---|
| EP | 2 333 517 A2 | 6/2011 |
| EP | 2 833 129 A1 | 2/2015 |
| WO | WO 2013/039468 A1 | 3/2013 |

OTHER PUBLICATIONS

Wenbln Xue, et al., "New Four-Band Electrode Fabrication to Measure in Situ Electrical Property of Conducting Polymers", Technical Notes, Analytical Chemistry, vol. 81, No. 6, Mar. 15, 2009, pp. 2364-2372.

French Preliminary Search Report dated Feb. 24, 2016 in French Application 15 53533, filed on Apr. 20, 2015 ( with English translation of categories of Cited Documents and Written Opinion).

Elizabeth W. Paul et al. "Resistance of Polyaniline Films as a Function of Electrochemical Potential and the Fabrication of Polyaniline-Based Microelectronic Devices", Journal of Physical Chemistry, vol. 89, 1985, 7 pages.

Erez Braun et al. "DNA-templated assembly and electrode attachment of a conducting silver wire", Letters to nature, vol. 391, 1998, 4 pages.

* cited by examiner

Section A-A

FIG. 6b

ELECTRONICAL DEVICE FOR MEASURING AT LEAST ONE ELECTRICAL CHARACTERISTIC OF AN OBJECT

FIELD OF THE INVENTION

The invention relates to a device and a method for measuring at least one electrical characteristic of an object.

It is intended preferentially for the characterization of objects of reduced size, micrometric or nanometric. These objects may notably partially consist or be obtained by biological material, particularly DNA, proteins, organic molecules, metallized DNA antibodies, nanotubes, etc.

A possible characterization in the determination of the contribution of the object to the flow of a current through a circuit closed by said object. It is thus possible to study the electrical transport of the object.

STATE OF THE RELATED ART

The prior art includes devices for characterizing objects using electrodes used to act as contact zones with the object for electrical conduction.

In this context, the publication by Elizabeth W. PAUL et al published in "*The Journal of Physical Chemistry*", vol. 89, No. 8 in 1985, entitled "*Resistance of Polyaniline films as a function of electrochemical potential and the fabrication of Polyaniline-based microelectronic devices*" describes a structure equipped with a series of parallel electrodes, of the same size and independent at the upper surface whereof an object made of polyaniline can be deposited. The quantity of the current applied to a given potential by means of the electrodes is dependent on the electrochemical potential of polyaniline and makes it possible to characterize the object made of this material. The measurement is merely a current measurement between two electrodes.

The measurement precision offered by this prior structure is limited. In particular, it does not account for the parasitic electrical phenomena occurring at the interface between the electrodes and the object to be characterized. It likewise does not offer the possibility of performing a statistical measurement of the current conducted by one or a plurality of nano-objects. Furthermore, the positioning of objects is difficult on such structures.

The present invention makes it possible to remedy all or part of the technical drawbacks currently known.

SUMMARY OF THE INVENTION

One aspect of embodiments of the invention relates to an electronic device for measuring at least one electrical characteristic of an object, comprising a supporting base provided with at least two measuring units each comprising at least two sets of electrodes with i integer greater than or equal to 2, each set of electrodes comprising a number mi of electrodes greater than or equal to one, the electrodes of a set of electrodes having a dimension in width, the electrodes of the sets of electrodes of the same measuring unit being interdigitated such that each electrode of one of the sets of electrodes Ji of said measuring unit is spaced by an inter-electrode distance from an electrode, of the other of the sets of electrodes Ji+1 of said measuring unit, which is adjacent thereto; the electrodes of the sets of electrodes of a measuring unit forming for said measuring unit, a zone for receiving at least one object, each object in this receiving zone defining a discontinuous contacting zone with the electrodes of the measuring unit, said contacting zone having a predetermined length according to the dimension in width (W) of the electrodes corresponding to the sum of the widths of the electrodes in contact with this object, and each receiving zone further comprising a discontinuous inter-electrode zone having a predetermined length according to the dimension in width (W) of the electrodes of said measuring unit; a measurement circuit connected to the sets of electrodes of each measuring unit configured to determine the current passing through the object; device wherein at least two measuring units differ from each other by the length of the contacting zones thereof and/or the length of the inter-electrode zones thereof.

A further aspect of embodiments of the invention relates to a method for measuring at least one electrical characteristic of an object, comprising:
  the use of a device;
  a step for placing an object on the contacting zone of a measuring unit and a step for measuring the current circulating between the sets of electrodes of said unit;
  a step for placing the object or an identical object on the contacting zone of a further measuring unit and a step for measuring the current circulating between the sets of electrodes of said further unit;
  an evaluation of the current passing through the object.

A potential benefit of the invention is that of enabling a differential measurement of the currents passing through objects via the electrodes so as to control, or even cancel out, the effects of parasitic phenomena such as the formation of parasitic currents at the contacts between the object and the electrodes. These parasitic currents, due to contact resistances, are taken into account differentially using a plurality of measuring units differing by the contact resistance caused thereby.

A further aspect of the invention is a method for manufacturing a measuring device.

A further aspect of the invention is that of being able to carry out a statistical measurement of nano-objects. A large number of units will be preferably manufactured on a substrate and a statistical study with a large number of items of information (W, G etc.) which can be analyzed.

A further aspect of the invention is that of favoring the deposition of small tools such as proteins. It is difficult to monitor the precise positioning, notably by depositing a liquid containing the nano-objects between two electrodes. The invention is thus of particular interest because, due to a large number of devices potentially manufactured on a substrate, the probability of at least one protein being positioned at best on the electrodes is increased.

The invention thus relates to an industrial aspect through the use of these electrodes on a substrate (examples: silicon with 100 mm, 200 mm or 300 mm wafers) for obtaining a large number of nano-objects on a conventional substrate suitable for industrial use.

A further aspect of the invention is a system comprising a device according to the invention and at least one object of a given type.

INTRODUCTION TO THE DRAWINGS

The attached drawings are given by way of examples and are not restrictive of the invention. They represent merely one embodiment of the invention and will make it possible to understand the invention easily.

DETAILED DESCRIPTION

Further aims and advantages will emerge during the following description presenting an illustrative but non-restrictive embodiment of the invention.

According to preferred but non-restrictive alternative embodiments, the invention is such that:

- the number of electrodes of each set of the same measurement unit may be equal to different. As such, although the figures represent the same number of electrodes for each set, it would be possible to have for example the set J1 (ref 2a FIG. 2) with a number m1 of electrodes less than the number m2 of electrodes of the set J2 (ref 1 FIG. 2) (for example m2=m1+1).
- said length of the contacting zone corresponds preferably to the sum of the widths (WJi) of the parts of the electrodes actually in contact with said object. In particular, the ends of the object not necessarily covering the entire width of an electrode, the width thereof will only be partially involved.
- the contacting zone may be less than the sum of the widths of all the electrodes of a measuring unit when the object does not cover all the electrodes of this unit. As such, some of the electrodes of a unit may not be taken into account in this contacting zone or only partially
- in each set of electrodes of each measuring unit, the dimension in width of the electrodes is identical.
- the length of the contacting zone of at least two measuring units differs by the width of the electrodes of at least one set of electrodes of each of said two measuring units.
- the length of the contacting zone of at least two measuring units differs by the number (m) of electrodes of the sets of electrodes thereof.
- in each set of electrodes of each measuring unit, the inter-electrode distance is identical.
- the lengths of the inter-electrode zones of at least two measuring units differ by the inter-electrode distances thereof;
- the measurement circuit comprises contact bumps, the sets of electrodes of the same measuring unit being connected to separate contact elements;
- the measurement circuit comprises at least one contact element connected to a plurality of sets of electrodes each belonging to a different measuring unit;
- at least one contact element is situated on a different face of the supporting base to a face whereon the measuring unit to which said at least one contact element is connected is situated, and in that the measurement circuit comprises a connection part, advantageously passing through the supporting base, between said at least one contact element of the measuring unit;
- the electrodes of the sets of electrodes of said at least one measuring unit are flush;
- the electrodes of the sets of electrodes of said at least one measuring unit are spaced by flush non-conductive portions on the face of the supporting base;
- the dimension in width (W) of the electrodes is less than 10 μm, and preferably less than 1 μm;
- the inter-electrode distance is between 1 nm and 10 μm, and preferably less than between 500 nm and 1 μm;
- the length of the contacting zone is less than 1 nm;
- the electrodes of the sets of electrodes of at least one measuring unit comprise an upper layer of Ruthenium;
- the supporting base comprises a first face provided with at least one measuring unit and a second face different to the first face, provided with at least one measuring unit;
- the measurement circuit comprises an electrical power supply and a part for measuring the current circulating between the sets of electrodes of the measuring units in the presence of an object on the contact zone of the measuring units.

The features mentioned above are merely optional.

A further aspect of the invention is a method for manufacturing a measurement device such that it comprises at least one of the following options:

- a filamentous object is used and the object is placed on the contacting zone of a measuring unit such that a dimension in length of the object is directed according to the dimension in width of the electrodes of said measuring unit;
- an object having a dimension less than 1 mm, and preferably less than 100 μm, is used;
- an object having a dimension in width less than 10 μm is used.

As a general rule, the invention makes it possible, by means of measuring units, to perform a measurement of electrical characteristics of an object, an electrical measurement being particularly able to be inferred from the contribution of a current passing through the object when the latter is placed so as to close a circuit between two sets of electrodes, the circuit then comprising an electrical power supply source and means for measuring current between the electrodes.

The invention notably makes it possible to characterize the electrical and conduction or contact properties of objects suitable for being used for a large number of devices used for example as sensors, object interconnections. The fields of application of these devices being for example microelectronics, medicine, automotive industry, agri-food, etc.

A preferred positioning consists of orienting the object transversally to the dimension in width of the electrodes. This is particularly preferable in the case of filamentous objects, denoting herein object having a high aspect ratio, for example greater than 10 or 50. These objects may further be micro- or nano-objects, i.e. at least one of the dimensions thereof is on a micrometric or nanometric scale, respectively. For example, the length of the object may be between 1 Å and 1 nm and more preferentially between 100 nm and 100 μm. The width or the diameter of the object may for example be between 1 nm and 10 μm. The object may in turn consist of one or a plurality of parts and thus be complex such as bio-inspired nano-objects derived from biological or living components. A plurality of objects may be measured simultaneously.

The filamentous aspect of the object is not restrictive and the invention notably also applies to spherical objects.

The object(s) are preferably solid under the measurement conditions and may be placed directly onto the units 20 without being dispersed in a fluid, or be supported by a fluid, notably a liquid.

In a first case, the object or objects, preferably solid, may be dispersed in a fluid, such as a solution, for the handling thereof. In this case, the current measurements may be performed in this fluid phase. However, preferentially, the fluid phase is removed before the measurements. For example, the object(s) are brought into contact with the measuring units by being carried by a solution (notably aqueous). Then drying removes the liquid phase such that the objects remain in the solid state without a liquid environment for the measurement phase.

In a further case, the object(s) are placed directly on the units 20 without using a fluid transport phase.

The device according to the invention is an electronic device in that it comprises electrical parts on a supporting base which may, preferably comprise a substrate for example made of semiconductor material, notably based on silicon. It may thus consist of a microelectronic device.

Hereinafter in the description, the following terms are used with the preferential definition associated therewith hereinafter:

electrodes: consist of electrically conductive devices, advantageously elongated in shape and accessible for contacting a part of an object to be characterized;

set of electrodes: denotes a series of at least one electrode, the electrodes being connected to a common connection, notably connected to one end of each electrode. A measuring unit whereon an object may be placed typically comprises two sets of electrodes. The latter are then interdigitated: each set of electrodes forms a comb type structure, the two combs being interlocked so as to alternate, according to the dimension in width of the electrodes, the electrodes of the first set and the second set. In one limit case, the interdigitation is limited to the juxtaposition of an electrode of a first set (which only comprises one electrode) and an electrode of a second set (which only comprises one electrode).

Figure 1:
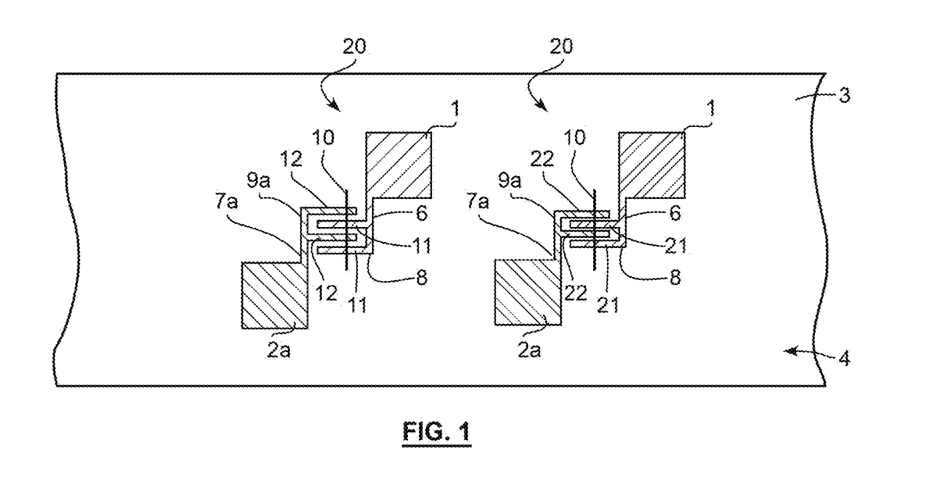
FIG. 1 is a top view of a face of a supporting base equipped with two measuring units according to the invention in one embodiment of the invention.

With reference to FIG. 1, an example representing two measuring units 20 is illustrated. The units 20 are herein independent structures formed on a first face 4 of a supporting base 3, for example obtained from a manufacturing process on a substrate made of silicon or another semiconductor material. Each unit 20 comprises two sets of electrodes. The electrodes 11 belong to a first set. They are electrically conductive and arranged in parallel along the longitudinal direction thereof, the electrodes 11 being advantageously rectilinear. They form a terminal of an electric circuit, open in the absence of an object to be measured, and closed when an object is placed on the measuring unit. For connection to the set of electrodes 11 to the rest of the circuit, it is possible to connect the proximal ends of the electrodes 11 to a comb bar 8 for example oriented transversally to the electrodes 11 and in turn electrically connected to a contact element 1 which can be used as a contact zone for a measurement by a measuring part of the electric circuit constructed overall. The contact element 1 may be remote from the set of electrodes 11. As such, an interconnection line 6, of variable shape and length, may be present between the electrodes 11 and the contact element 1.

In the illustration in FIG. 1, the contact element 1 is accessible on the first face 4 where the electrodes 11 are situated. An alternative configuration consists of arranging the contact element 1 on another face of the supporting base 3, for example an opposite face (second face 5 described hereinafter with reference to FIG. 5a for example) to the first face 4. In this case, the interconnection line 6 may pass through the supporting base 3, according to the thickness thereof. Through vias, frequently referred to as TSV (Through Silicon Via) may be used for silicon-based substrates.

The set of electrodes 11 thus forms a first comb and the upper surface thereof, i.e. parallel to the surface of the first face 4, offers a zone for placing objects to be characterized, with possible electrical conduction.

The measuring unit 20 then comprises a further set of electrodes 12 complementary to the set of electrodes 11, in that they form a further electrical connection terminal of an object placed on the measuring unit 20.

Although it is not absolutely necessary, the set of electrodes 12 may be similar to the set of electrodes 11. The set of electrodes 12 may thus also notably be connected to a contact element 2a, by an interconnection line 7a, a comb bar 9a serving as a common electrical point at one end of the electrodes 12.

The electrodes 12 are organized in an interdigitated manner with the electrodes 11 such that along a transversal direction to the length of the electrodes 11, 12 (corresponding to the dimension in width), the electrodes 11 and 12 are alternated with an inter-electrode gap in each case. The interdigitation should make it possible to place an object, transversally to the length of the electrodes, and form contacts between at least one electrode 11 and an electrode 12, so as to close the part of the electric circuit between the two sets of electrodes 11, 12.

Advantageously, at least one of the sets of electrodes comprises more than one electrode 11 or 12, but one extreme case consists of using two sets of one single electrode each. The interdigitation is then a juxtaposition of the electrodes 11, 12 along a width W.

Preferably, for a given set of electrodes 11, 12, the width W of the electrodes 11, 12 is fixed. The length thereof is also advantageously fixed. The width W of the electrodes 11, 12 may be different between the two sets of electrodes forming a measuring unit 20.

In the case of FIG. 1, two units 20 have two sets of two electrodes 11, 12.

The interdigitation produces a gap between the electrodes of a measuring unit 20. Preferably, this gap has the same length along the dimension in width W of the electrodes. It is also referred to herein as the inter-electrode distance G.

It is understood that, when an object is placed on the measuring unit 20, transversally to the electrodes 11, 12, it comes into contact with a plurality of electrodes 11, 12 if the dimension thereof is greater than the distance G. The object may, preferably, come into contact with all the electrodes 11, 12 of the measuring unit 20. Such a contact, in a plurality of zones of the object, according to the dimension in width of the electrodes 11, 12, produces a discontinuous contacting zone in which a part of each electrode 11, 12 participates. The length of this contacting zone is thus defined by the sum of the widths of the electrodes 11, 12. The width of the contacting zone is dependent on the dimension of the object along the length of the electrodes 11, 12. This combination of contact zone dimensions defines an overall contact area.

This area is all the greater if the width W of the electrodes is high and/or the number m of electrodes of the sets is high. This is also verified, even if the object is not strictly oriented perpendicular to the electrodes.

When an object is placed on the measuring unit 20, transversally to the electrodes 11, 12, if it comes into contact with merely a portion of the electrodes, the contact zone will be smaller than the sum of the widths of the electrodes. This case is particularly observed at the ends of the nano-object as the start and end of the nano-object is not always in contact over the entire width of the electrode but merely over a part of the electrode. It is of particular interest in this case to perform a morphological characterization, by imaging such as SEM (scanning electron microscope) or TEM (transmission electron microscope) or AFM (atomic force microscope) in order to determine precisely the value of the contact zone. It can be noted that the reduction of the values G, W proposed in the invention makes it possible to reduce the uncertainty on these specific zones.

During a characterization, an object type is generally to be characterized. A single object may be sufficient and in this case it will be contacted with a plurality of units 20; a plurality of objects may also be used, for example two objects of a given type placed on a zone for receiving a different unit. The term object type means that the objects have at least one identical feature (notably material and/or length and/or width) such that they reflect a common nature and sufficient similarity to enable a characterization of the object type by characterizing each thereof. However, it is not excluded that the objects of a type vary somewhat relative to one another. For example, they may be of different lengths, but for example each time sufficient to cooperate with all or a majority of the electrodes of the measuring units.

A characterization may be performed with contact of an object with at least two electrodes of two units, the object for example overlapping between these units. Measurement will be particularly possible with greater cooperation between the object and the units 20: in the illustration in FIG. 2, the object may be in contact with all the electrodes of the median unit 20 and in contact with merely part of the electrodes of at least one of the other units surrounding same. The object to be measured is preferentially longer than the series of juxtaposed units 20 so as to obtain, as in FIG. 2, contact on all the electrodes.

Again with reference to FIG. 2, it is possible that the units all have widths of zones for receiving objects of the same length (along a long direction of the electrodes perpendicular to the width W). In this case, it is advisable to align the units such that the receiving zones are sequenced as in FIG. 2. Advantageously, the distance between two measuring units 20 along the juxtaposition direction is less than 10 times, or 5 times (and preferably 2 times) the greatest value of W throughout these juxtaposed units 20.

When an object is placed on the measuring unit 20, a current source makes it possible to flow current through the object. This is referred to as electrical characterization of a nano-object. The electrical characterization is defined for example by the parameters such as the current, electron flow through a section of a nano-object, electrical conduction or resistance. This electrical characterization may also be suitable for studying the transport properties and the behavior of the nano-object. In addition to these different parameters, the current passing through is influenced by a parasitic current, a portion whereof is due to the resistance of the working electrodes and to the resistance of the other portions involved in the measurement circuit such as the line resistance or that of the pads or contact elements. This parasitic current portion may be determined by making an electrical measurement of the unit in the absence of the object, for example a so-called "4-point" measurement. A further portion of the parasitic current is due to the contact resistance between the electrode and the object.

This resistance is proportional to the contact area between the object and the electrodes (thus proportional to the length of the contacting zone which is dependent on the number of electrodes m and the width of the electrodes). Relative to the length of the object, it is also necessary to account for the length of the inter-electrode zone which the complementary value of that of the contacting zone. As such, according to the invention, an adjustment is made of the value of at least one parameter among the number of electrodes m, the width of the electrodes W and the distance separating the electrodes in order to vary, from one measuring unit to another the value of the contact resistance and, carrying the value of the parasitic current. Subsequently, given the parasitic current, it is possible to determine the current passing through the object or any object of the same type.

Consequently, the invention performs a differential measurement using at least two different measuring units 20 so as to have different parasitic current values. Advantageously, the same electrical parameters are used in each measuring unit (particularly current value) for this measurement. Preferably, the electrodes of all the units are of the same material, or materials having identical electrical resistivity properties. Preferably, the electrodes of the measuring units merely differ by the number thereof and/or the value of G and/or the value of W.

In a first case, only the value of the width of the electrodes between two otherwise equivalent units is modified. The current variation measured corresponds to a parasitic current variation which can thus be determined.

In a further case, at the same electrode width W of both units, the inter-electrode gap thereof is modified. The current differential measured is a current differential through the electrodes.

A further possibility consists of changing the number of electrodes with the same effect as in the first case on the modification of the contact area.

The representation in FIG. 1 shows the case of a modification of inter-electrode distance G between the units 20, the other parameters being identical (same width W for the electrodes 11, 12, 21, 22 and two electrodes per set of electrodes). The units 20 are herein of separate structures.

Figure 2:
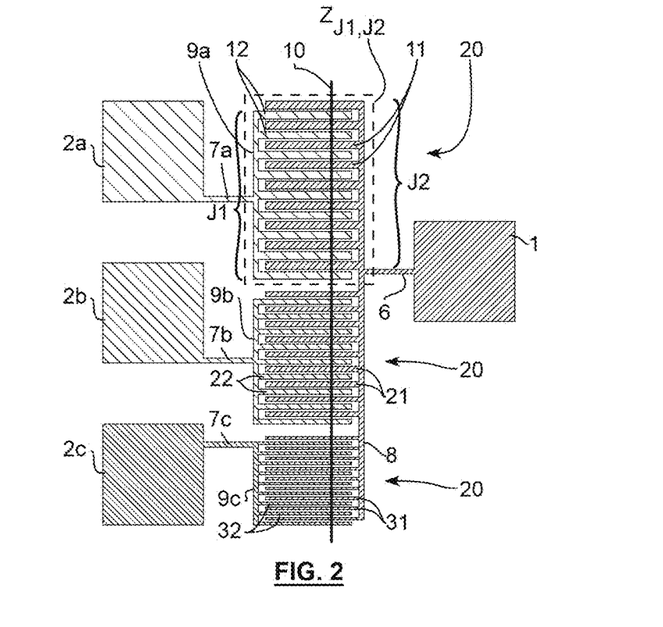
FIG. 2 is a top view of a face of a supporting base equipped with two measuring units according to the invention in a further embodiment.

More complex designs are possible such as in FIG. 2 with a plurality of units 20 each having a set of electrodes connected to a contact element 1 as the three grouped units have herein different inter-electrode distances so as to measure the object over a plurality of distances. This is particularly suitable for bio-inspired nano-objects, which are heterogeneous such as a protein with a plurality of functions over the length thereof. In the case in FIG. 2, a plurality of units 20 are juxtaposed so as to extend in continuity along a preferred direction which may be that of the width of the electrodes.

Notably in the case of FIG. 2, the positioning in series of the different measuring units 20 differing by the electrodes thereof (parameter W and/or G and/or number of electrodes) and the differential measurement of the same nano-object on electrodes makes it possible to trace back to the contribution of the parameters involved in electrical conduction. It is thus possible to obtain genuine electrical properties of the object or a portion of the object since the unnecessary contributions (such as the surface contact and/or resistivity of the metal of the electrodes, etc.) have been subtracted.

It should be noted that in FIG. 2, not only the units 20 are in a row along a preferred direction for placing an object, but also benefits from pooling of a connection to the measuring unit, by sets of electrodes placed in series, the opposite sets of electrodes remaining connected separately to the measuring unit. As such, in one embodiment, at least part of the measuring units 20 are arranged in series, with respectively, a set of electrodes connected to the same contact element and the other sets of electrodes connected to separate contact elements.

It should be noted that it is also possible to vary the parameters W and m therein.

The compact size of this device is also revealed by the presence of four contact elements 1, 2a, 2b, 2c merely with four interconnection lines 6, 7a, 7b, 7c, for six sets of electrodes in total.

The sets of electrodes being close together, the measurement conditions are similar (such as quasi-simultaneity, humidity, pressure, brightness) all on the same material.

This design may be used for proteins having a length of 100 nm or a complex object formed from a plurality of elementary objects (such as grouped nano-objects). With a high number of electrodes m, it is possible to characterize numerous sections of the object and obtain a mean value thereof.

Figure 3:
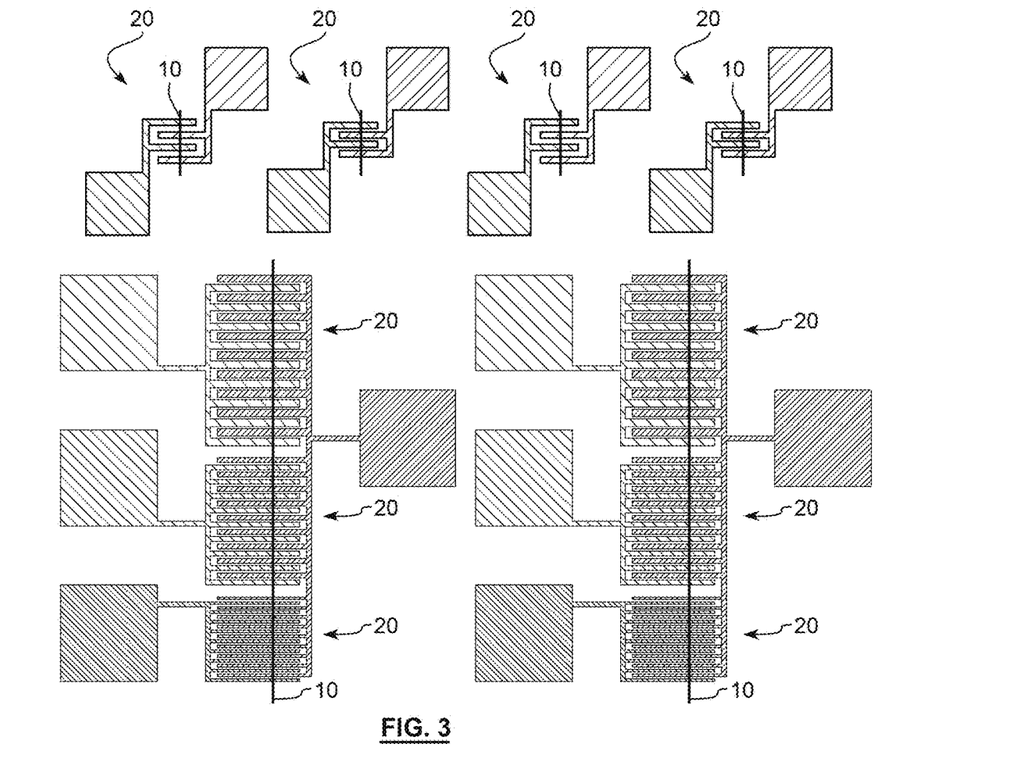
FIG. 3 is a top view of a supporting base integrating a plurality of measuring units of different designs.

The number of measuring units 20 is not restricted according to the invention. Multiplying same makes it possible to make measurements in parallel on a plurality of objects of the same type (same material, same shape notably). This is illustrated by FIG. 3 with ten units. Four thereof are similar to those in FIG. 1, for a measurement of a first object type. Six others are of the embodiment in FIG. 2, having multiple parameters, applied to another object type.

Figure 4:
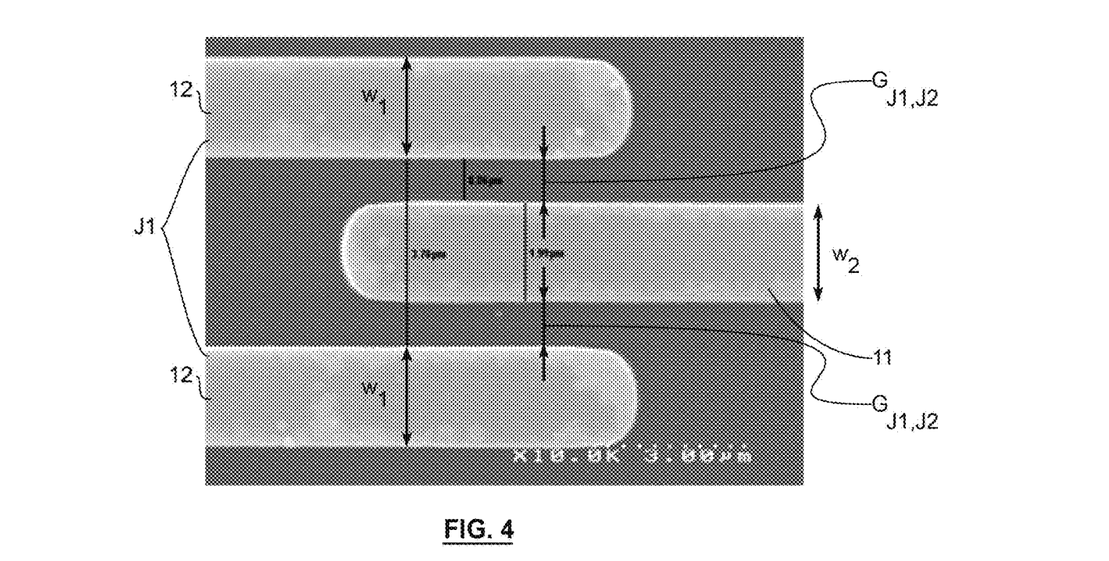
FIG. 4 is a microscope view illustrating interdigitated electrodes of two electrodes.

FIG. 4 illustrates a detailed microscope view of three adjacent electrodes 11, 12. According to this example, the following parameters are possible:
    width of the patterns W of the electrodes 11, 12 between 1 nm and 10 µm, but typically in this example the width is 1.99 µm.
    Gap G between two electrodes 11, 12 between 100 nm and 10 µm, but typically between 500 nm and 1 µm, in this example the width is 0.86 µm.
    Gap between three electrodes (between two electrodes of the same set) between 100 nm and 10 µm, but typically in this example the spacing is 3.76 µm.

This structure makes it possible herein to characterize a bio-inspired object over distances of 3.76 µm and 0.86 µm accounting for an electrode contact resistance of width 1.99 µm using the design in FIG. 1.

A further aspect of the invention is a method for manufacturing a measurement device using a substrate 50. FIGS. 5a to 5h show an example thereof.

The height of the electrodes will be adjusted according to the object to be characterized and the object/supporting base contact resistance constraints. The electrode height will be preferably between 10 nm and several tens of micrometers. Typically, the height will be 200 nm but may vary for example between 10 nm and 100 µm.

Figure 5A:
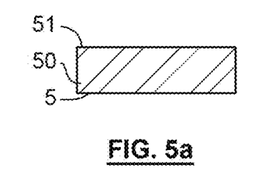
FIGS. 5a, 5b, 5c, 5d, 5e, 5f, 5g, 5h, 5i, 5j, and 5k represent schematically successive steps of a possibility of a method for manufacturing a device.

FIG. 5a shows a wafer of semiconductor material, such as silicon, suitable for forming the initial substrate 50 of the manufacturing method. It comprises a first face 51 using which a measuring unit will be manufactured, and an opposite face which will form the second face 5 of the device.

Figure 5B:
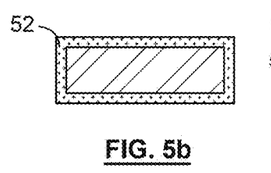

An optional step shown in FIG. 5b consists of forming an oxide layer 52, particularly of silicon, about the substrate 50, to protect the surfaces during a subsequent ion implantation step, also optional. The oxidation is for example obtained from a heat treatment such as annealing in an oxygen atmosphere or be performed by deposition.

Figure 5C:
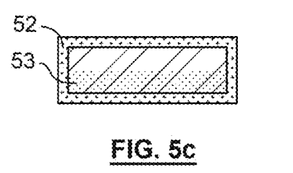

The implantation is represented schematically in zone 53 in FIG. 5c. It may enable more effective contact by the rear face 5. It may be performed by p or n type doping, for example with dopant concentrations between $10^{16}$ and $10^{20}$ at/cm$^3$ followed by activation annealing.

Figure 5D:
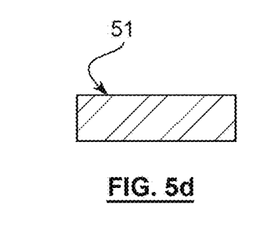
Figure 5E:
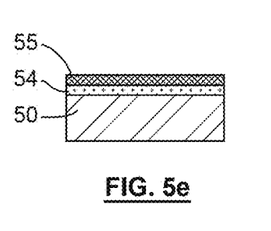

The oxide layer 52 obtained from FIG. 5b may be removed, at least in part, as in FIG. 5d. Etching, dry or wet, may be suitable. This step is also optional.

Then the electrically conductive material(s) to be used to form the sets of electrodes and any other associated conductive part, are deposited after positioning an insulating layer 54 (such as $SiO_2$) if the substrate is conductive. The layer 54 may be grown expitaxially or deposited notably by a conventional vapor phase deposition technique, from a few nanometers to several microns typically. $SiH_4$ may also be used.

For the conductive part, a bonding layer 55 for creating the conductive layer is preferably deposited. It is possible to use for example a titanium layer deposited using the PVD (physical vapor deposition) technique or electrolysis. The thickness of the layer will be for example of the order of a few nanometers to several microns in thickness but typically a layer of 10 nm of titanium is sufficient.

Figure 5F:
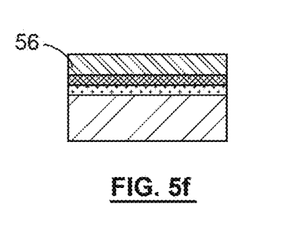

In FIG. 5f, the conductive layer 56 is deposited using various techniques well known to those skilled in the art typically by PVD, electrolysis or evaporation. The materials used may be platinum, gold, but preferentially a multi-layer will be used, one whereof consists of Ruthenium. The thicknesses will be of the order of a few nanometers to a few microns. Preferentially, two 200 nm layers consisting of gold will be deposited followed by one 50 nm layer of Ruthenium.

Ruthenium makes it possible to obtain perfectly straight edges and thus reduce the gap between two electrodes, due to the anisotropy of the etching thereof.

Figure 5G:
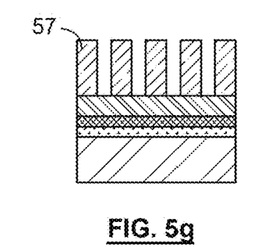

As can be seen in FIG. 5g, mask patterns 57 are created so as to obtain electrodes of very small widths (for example 100 nm to 10 µm but typically 1 µm). The height of the electrodes will be adjusted according to the nano-object or other object to be characterized and contact resistance stresses of the object or the supporting base. The electrode height will be between 10 nm and several tens of micrometers. Typically, the height will be 200 nm.

Figure 5H:
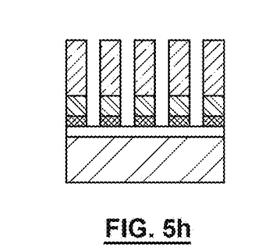
Figure 5I:
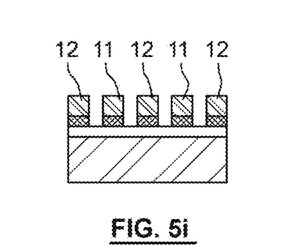

In FIGS. 5h and 5i, etching of the conductive layer 55, 56 is performed according to the patterns created and the resin deposited in the step in FIG. 5g is removed.

Figure 5J:
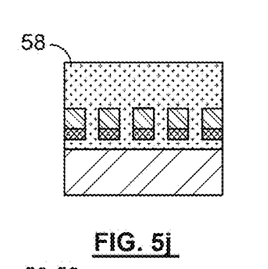

Then, the gap between the electrodes is filled with an oxide. It is possible for example to deposit an insulating layer 58 of at least the height of the electrodes. This layer will be deposited using conventional techniques such as PECVD (plasma-enhanced chemical vapor deposition), LPCVD (low-pressure chemical vapor deposition) and other techniques well-known to those skilled in the art. For example, a layer of silicon oxide of a height at least equal to the height of the electrodes will be deposited on a silicon substrate by PECVD. According to one example, the thickness of oxide between the electrodes will be at least 200 nm, equivalent to the height of the electrodes of 200 nm. This can be seen in FIG. 5j.

In the case of a deposition on the entire surface (conforming deposition), an insulating layer 58 may be present on the electrodes. A partial removal step, by polishing such as Chemical Mechanical Polishing (CMP) or dry and/or wet etching will be performed in order to strip the electrodes. For example, during a deposition of 500 nm of oxide by PECVD on a silicon substrate comprising an electrode height of 200 nm, 300 nm of oxide will be removed. The result can be seen in FIG. 5k.

As mentioned above, the conductive layer 58 may be made of a plurality of sublayers of different materials.

Figure 5K:
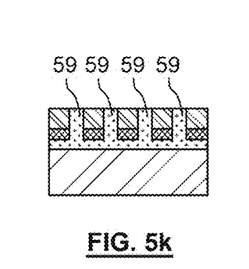
Figure 5L:
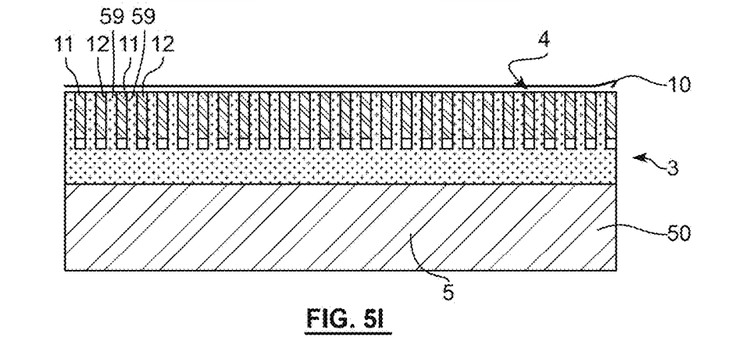
FIGS. 5l and 5m show two variants of results.

The result in FIG. 5k shows electrodes flush with the first face 4 of the device constructed in this manner. Similarly, non-conductive inter-electrode portions 59 are flush with the first face 4. This offers plane contact for the object to be measured, as seen in FIG. 5l.

It should also be noted in this figure that a large number m of electrodes provides multiple measurement sections of the object.

Figures 5M, 6A:
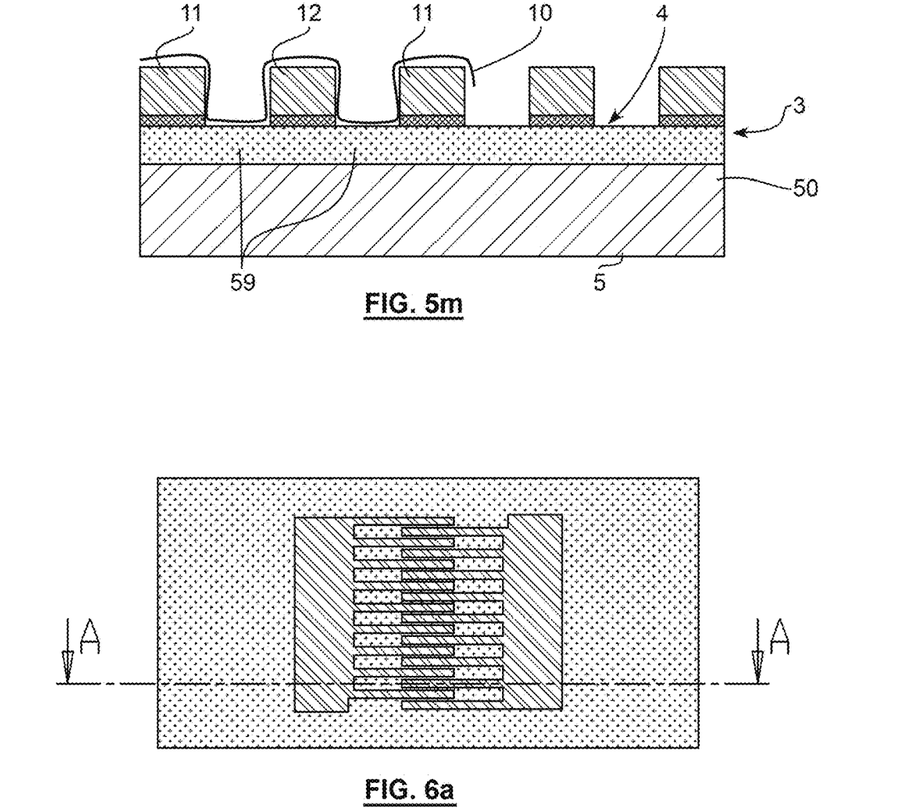
FIG. 6a shows schematically a top view of an example of embodiment of electrodes for a measuring unit.

In one alternative embodiment illustrated in FIG. 5m, the non-conductive portions 59 are at a lower height level than that of the electrodes 11, 12 such that the object 10, particularly if it is filamentous such as a filamentous protein, is deformed along the thickness of the substrate, and not in the plane of the upper face of the electrodes 11, 12. This case is generally less favorable than that in FIG. 5l. The embodiment flush with the electrodes 11, 12 relative to the non-conductive portions, such that the whole is in the plane of the face of the supporting base 3 is thus preferred. This feature of flush formation of the electrodes 11, 12 may further be implemented independently of the other aspects of the invention, for example those associated with the differential measurement with a plurality of measuring units. As such, the invention also relates to a device for measuring an electrical characteristic of an object comprising one measuring unit at least, with two sets of electrodes wherein the upper surface is flush relative to the part of the face of the supporting base surrounding the electrodes, including conductive inter-electrode portions.

Figure 6B:
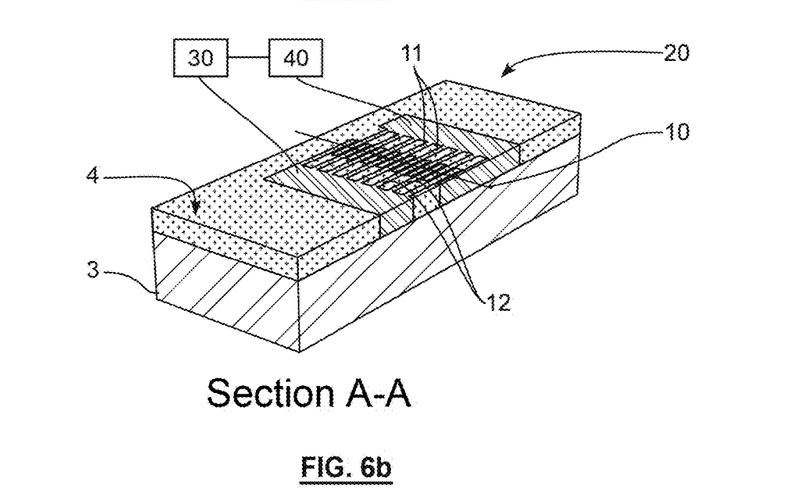
FIG. 6b shows a sectional perspective view thereof along the line AA in FIG. 6a and represents a measurement circuit schematically.

This flush mounting principle is also illustrated in FIGS. 6a and 6b where the insulator surrounds the electrodes 11, 12. FIG. 6b also shows schematically the measurement circuit.

The measurement circuit typically comprises an electrical power supply source 30 and at least one system 40 for measuring electrical quantities, particularly currents, these elements being connected in an optionally fixed manner to the electrodes, preferably via contact elements 1, 2a, 2b, 2c (not seen in FIG. 6b). It is thus possible, with a measurement of the current at the contact elements 1, 2a, 2b, 2c, to evaluate the electrical contribution of the object to the currents measured, advantageously accounting for the parasitic currents.

The currents are frequently low for nano-objects, for example between $5 \cdot 10^{-9}$ A mad $5 \cdot 10^{-8}$ A for an amyloid protein.

According to one measurement method according to the invention, at least one object is placed on a measuring unit taking care to ensure that it has a transversal orientation to the length of the electrodes. The positioning may take place by depositing drops of solution wherein the object(s) to be characterized are present. The device per se may also be immersed, at least by one face where the measuring units are situated, in a solution containing the objects.

The presence of multiple measuring units makes it possible to increase the probability of correct positioning of the objects on the units. When the objects placed on the units are identical (particularly same material and same size), simultaneous measurements are possible.

The invention claimed is:

1. An electronic device for measuring at least one electrical characteristic of an object, the electronic device comprising:
a supporting base provided with at least two measuring units each comprising at least two sets of electrodes with i integer greater than or equal to 2, each set of electrodes comprising a number mi of electrodes greater than or equal to one, the electrodes of a set Ji of electrodes having a dimension in width, the electrodes of the sets of electrodes of a same measuring unit being interdigitated such that each electrode of one of the sets of electrodes Ji of said measuring unit is spaced by an inter-electrode distance from an electrode of an other of the sets of electrodes Ji+1 of said measuring unit, which is adjacent thereto, the electrodes of the sets of electrodes of a measuring unit forming for said measuring unit, a receiving zone for receiving the object defining, in the receiving zone, a discontinuous contacting zone with the electrodes of the measuring unit, said contacting zone having a predetermined length according to the dimension in width of the electrodes corresponding to a sum of widths of the electrodes in contact with the object, and each receiving zone further comprising a discontinuous inter-electrode zone having a predetermined length according to the dimension in width of the electrodes of said measuring unit; and
a measurement circuit connected to the sets of electrodes of each measuring unit to determine a current passing through the object,
wherein at least two measuring units differ from each other by a length of the contacting zones thereof and/or a length of the inter-electrode zones thereof, the measurement circuit being configured to determine a difference in current values of the at least two measuring units and to determine a differential electrical contact resistance value between the object and the electrodes of each of the measuring units.

2. The device according to claim 1, wherein, for at least one measuring unit, at least one set of electrodes comprises a number mi of electrodes greater than or equal to 2, and wherein at least two electrodes of said at least one set of electrodes, are in contact with the object.

3. The device according to claim 1, wherein each measuring unit has a dimension in width less than or equal to a dimension in length of the object.

4. The device according to claim 1, wherein the at least two measuring units are juxtaposed along the dimension in width.

5. The device according to claim 1, wherein, in each set of electrodes of each measuring unit, the dimension in width of the electrodes is identical, and wherein the length of the contacting zone of at least two measuring units differs by the width of the electrodes of at least one set of electrodes of said at least two measuring units.

6. The device according to claim 1, wherein the length of the contacting zone of at least two measuring units differs by the number of electrodes of the sets of electrodes thereof.

7. The device according to claim 1, wherein, in each set of electrodes of each measuring unit, the inter-electrode distance is identical, and wherein the lengths of the inter-electrode zones of at least two measuring units differ by the inter-electrode distances thereof.

8. The device according to claim 1, wherein the measurement circuit comprises contact elements, the sets of electrodes of the same measuring unit being connected to separate contact elements, and wherein the measurement circuit comprises at least one contact element connected to a plurality of sets of electrodes each belonging to a different measuring unit.

9. The device according to claim 8, wherein at least one contact element is situated on a supporting base face differing from a face whereon the measuring unit is situated to which said at least one contact element is connected, and wherein the measurement circuit comprises a connection part between said at least one contact element of the measuring unit passing through the supporting base.

10. The device according to claim 1, wherein the electrodes of the sets of electrodes of said at least one measuring unit are flush on one face of the supporting base, and wherein the electrodes of the sets of electrodes of said at least one measuring unit are spaced by flush non-conductive portions on the face of the supporting base.

11. The device according to claim 1, wherein the dimension in width of the electrodes is less than 1 µm and/or the inter-electrode distance is between 500 nm and 1 µm.

12. The device according to claim 1, wherein the supporting base comprises a first face provided with at least one measuring unit and a second face different to the first face, provided with at least one measuring unit.

13. A system comprising:
the device according to claim 1; and
the object, the at least two measuring units receiving the object on the respective receiving zone thereof.

14. A method for measuring at least one electrical characteristic of an object, using a device that comprises a supporting base provided with at least two measuring units each comprising at least two sets of electrodes Ji with i integer greater than or equal to 2, each set of electrodes comprising a number mi of electrodes greater than or equal to one, the electrodes of a set Ji of electrodes having a dimension in width, the electrodes of the sets of electrodes of a same measuring unit being interdigitated such that each electrode of one of the sets of electrodes Ji of said measuring unit is spaced by an inter-electrode distance from an electrode of an other of the sets of electrodes Ji+1 of said measuring unit, which is adjacent thereto, the electrodes of the sets of electrodes of a measuring unit forming for said measuring unit, a receiving zone for receiving the object defining, in the receiving zone, a discontinuous contacting zone with the electrodes of the measuring unit said contacting zone having a predetermined length according to the dimension in width of the electrodes corresponding to a sum of widths of the electrodes in contact with the object, and each receiving zone further comprising a discontinuous inter-electrode zone having a predetermined length according to the dimension in width of the electrodes of said measuring unit; and a measurement circuit connected to the sets of electrodes of each measuring unit to determine a current passing through the object, wherein at least two measuring units differ from each other by a length of the contacting zones thereof and/or a length of the inter-electrode zones thereof, the measurement circuit being configured to determine a difference in current values of the at least two measuring units and to determine a differential electrical contact resistance value between the object and the electrodes of each of the measuring units, the method comprising:
placing the object of the zone for receiving a measuring unit of the at least two measuring units and measuring the current circulating between the sets of electrodes of said measuring unit;
placing the object on the zone for receiving a further measuring unit of the at least two measuring units and measuring the current circulating between the sets of electrodes of said further measuring unit;
determining a difference in the current values of the measuring units and determining a differential contact resistance value between the object and the electrodes of each of the measuring units; and
evaluating the current passing through the object on the basis of the current measurements made in the preceding steps.

15. The method according to claim 14, wherein the object is in a solid state.

16. The method according to claim 14, wherein the at least two measuring units of the device are juxtaposed along the dimension in width and the object is placed simultaneously on the at least two juxtaposed measuring units.

17. A method for measuring at least one electrical characteristic of an object, using a device that comprises a supporting base provided with at least two measuring units each comprising at least two sets of electrodes Ji with i integer greater than or equal to 2, each set of electrodes comprising a number mi of electrodes greater than or equal to one, the electrodes of a set Ji of electrodes having a dimension in width, the electrodes of the sets of electrodes of a same measuring unit being interdigitated such that each electrode of one of the sets of electrodes Ji of said measuring unit is spaced by an inter-electrode distance from an electrode of an other of the sets of electrodes Ji+1 of said measuring unit, which is adjacent thereto, the electrodes of the sets of electrodes of a measuring unit forming for said measuring unit, a receiving zone for receiving the object defining, in the receiving zone, a discontinuous contacting zone with the electrodes of the measuring unit, said contacting zone having a predetermined length according to the dimension in width of the electrodes corresponding to a sum of widths of the electrodes in contact with the object, and each receiving zone further comprising a discontinuous inter-electrode zone having a predetermined length according to the dimension in width of the electrodes of said measuring unit; and a measurement circuit connected to the sets of electrodes of each measuring unit to determine a current passing through the object, wherein at least two measuring units differ from each other by a length of the contacting zones thereof and/or a length of the inter-electrode zones thereof, the measurement circuit being configured to determine a difference in current values of the at least two measuring units and to determine a differential electrical contact resistance value between the object and the electrodes of each of the measuring units, and wherein each measuring unit has a dimension in width less than or equal to a dimension in length of the object, the method comprising:
placing the object of the zone for receiving a measuring unit of the at least two measuring units and measuring the current circulating between the sets of electrodes of said measuring unit;
placing the object on the zone for receiving a further measuring unit of the at least two measuring units and measuring the current circulating between the sets of electrodes of said further measuring unit;
determining a difference in the current values of the measuring units and determining a differential contact resistance value between the object and the electrodes of each of the measuring units; and
evaluating the current passing through the object on the basis of the current measurements made in the preceding steps.

* * * * *